US00PP13929P29

(12) United States Plant Patent
Jepsen

(10) Patent No.: US PP13,929 P2
(45) Date of Patent: Jul. 1, 2003

(54) KALANCHOE PLANT NAMED 'WHITE CORA'

(75) Inventor: Knud Jepsen, Hinnerup (DK)

(73) Assignee: Kund Jepsen A/S, Hinnerup (DK)

( * ) Notice: Subject to any disclaimer, the term of this patent is extended or adjusted under 35 U.S.C. 154(b) by 0 days.

(21) Appl. No.: 10/158,964

(22) Filed: May 31, 2002

(51) Int. Cl.[7] ..... A01H 5/00

(52) U.S. Cl. ..... Plt./336

(58) Field of Search ..... Plt./336

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Kalanchoe plant named 'White Cora', characterized by its upright and compact plant habit; dark green-colored leaves; large white-colored flowers; and excellent postproduction longevity.

1 Drawing Sheet

BOTANICAL CLASSIFICATION/CULTIVAR DESIGNATION

*Kalanchoe blossfeldiana* cultivar White Cora.

BACKGROUND OF THE INVENTION

The present invention relates to a new and distinct cultivar of Kalanchoe plant, botanically known as *Kalanchoe blossfeldiana*, and hereinafter referred to by the name 'White Cora'.

The new Kalanchoe is a product of a planned breeding program conducted by the Inventor in Hinnerup, Denmark. The objective of the breeding program was to create new freely-flowering Kalanchoe cultivars with compact plant habit and excellent postproduction longevity.

The new Kalanchoe is a naturally-occurring whole plant mutation of the *Kalanchoe blossfeldiana* cultivar Cora, disclosed in U.S. Plant Pat. No. 12,301. The cultivar White Cora was discovered and selected by the Inventor as a flowering plant within a population of plants of the cultivar Cora in a controlled environment in Hinnerup, Denmark.

Asexual reproduction of the new Kalanchoe by terminal cuttings taken at Hinnerup, Denmark, by the Inventor, has shown that the unique features of this new Kalanchoe are stable and reproduced true to type in successive generations.

BRIEF SUMMARY OF THE INVENTION

The cultivar White Cora has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'White Cora'. These characteristics in combination distinguish 'White Cora' as a new and distinct cultivar:

1. Upright and compact plant habit.
2. Dark green-colored leaves.
3. Large white-colored flowers.
4. Excellent postproduction longevity.

Plants of the new Kalanchoe are most similar to plants of the cultivar Cora and differ primarily from plants of the cultivar Cora in flower color.

BRIEF DESCRIPTION OF THE PHOTOGRAPHS

The accompanying colored photographs illustrate the overall appearance of the new Kalanchoe, showing the colors as true as it is reasonably possible to obtain in colored reproductions of this type. Colors in the photographs may differ slightly from the color values cited in the detailed botanical description which accurately describe the colors of the new Kalanchoe. The photographs were taken under diffuse natural light conditions on a sunny day at approximately noon in Hinnerup, Denmark.

The photograph at the top of the sheet comprises a side perspective view of a typical potted plant of 'White Cora'.

The photograph at the bottom of the sheet is a close-up view of the following: side and top perspective views of a typical flowering cyme and top perspective views of immature and fully expanded floral leaves of 'White Cora'.

DETAILED BOTANICAL DESCRIPTION

In the following description, color references are made to The Royal Horticultural Society Colour Chart, 1995 Edition, except where general terms of ordinary dictionary significance are used. Plants used in the photographs and for the following observations and measurements were grown in Hinnerup, Denmark, under commercial practice in a glass-covered greenhouse for about 10 weeks after the start of short day/long night photoperiodic treatment with average temperatures of 20° C. Plants used in the description and photographs were not pinched. Unless otherwise specified, the leaf description represents leaves from a vegetative plant.

Botanical classification: *Kalanchoe blossfeldiana* cultivar White Cora.

Parentage: Naturally-occurring whole plant mutation of *Kalanchoe blossfeldiana* cultivar Cora, disclosed in U.S. Plant Pat. No. 12,301.

Propagation:

*Type cutting.*—Terminal cuttings.

*Time to initiate roots.*—About 14 days.

*Root description.*—Numerous, fine, fibrous, and well-branched.

Plant description:

*Form.*—Upright and compact plant habit with numerous compound cymes; freely flowering. Actual plant shape will depend on whether or not plants are pinched (apical terminals removed). Finished plant size is appropriate for one plant per 9 to 10-cm container or three plants per 13-cm container.

*Branching habit.*—Freely branching. Pinching (removal of terminal apex) is not required but will enhance lateral branch development.

*Plant height at flowering.*—About 25 cm.

*Plant diameter at flowering.*—About 22 cm.

*Foliage description.*—Leaves simple, opposite, generally symmetrical. Size: Leaf size is reduced after floral induction. Vegetative plants: Length: About 8 cm. Width: About 7 cm. Reproductive plants: Length: About 6.5 cm. Width: About 5.5 cm. Shape: Oval. Apex: Obtuse. Base: Obtuse with truncate tendencies. Margin: Crenate; undulate. Aspect: Slightly concave. Texture: Leathery, glabrous, succulent, rugose. Color: Young foliage, upper surface: 137B, glossy. Young foliage, lower surface: 137C. Mature foliage, upper surface: 147A, glossy. Mature foliage, lower surface: 147B.

Flower description:

*Flower type and habit.*—Single flowers arranged in compound dichasial cymes that arise from leaf axils. Upright flowering stems. Freely flowering. Flowers persistent.

*Natural flowering season.*—Late autumn/winter/early spring; flower initiation and development can be induced under short day/long night conditions.

*Time to flower.*—In the summer with 20° C. growing temperatures, about 9.5 weeks of short day/long night conditions are required to produce flowering plants. During the winter with supplemental lighting and 20° C. growing temperatures, about 10.5 weeks of short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About 1.5 weeks after the first flower has opened, 50% of the remaining flowers are open.

*Post-production longevity.*—Plants of the new Kalanchoe maintain good leaf and flower substance for at least five weeks under interior environmental conditions.

*Flower diameter.*—About 2 cm.

*Quantity.*—Very freely flowering, at least 250 flowers per plant.

*Flower buds.*—Shape: Narrowly oblong. Length: About 1.4 cm. Width: About 4 mm. Color: 160C.

*Petals.*—Quantity: Four fused at base. Length: About 9 mm. Shape: Round obovate. Apex: Cuspidate. Margin: Entire. Texture: Glabrous, smooth and satiny. Color: Upper surface: Initially 4C becoming closest to 155D with subsequent development. Lower surface: Closest to 155D.

*Reproductive organs.*—Stamens: Stamen number: Eight. Anther shape: Slightly oblong. Filament color: Green. Pollen color: Yellow. Pistils: Pistil number: Four. Style color: Green. Stigma shape: Round. Ovaries: Superior and four-celled. Ovary size: About 5 mm by 1 mm. Ovary color: Light green.

*Seed/fruit.*—Seed and fruit production has not been observed.

Disease resistance: Resistance to known Kalanchoe diseases has not been observed on plants of the new Kalanchoe grown under commercial greenhouse conditions.

It is claimed:

1. A new and distinct cultivar of Kalanchoe plant named 'White Cora', as illustrated and described.

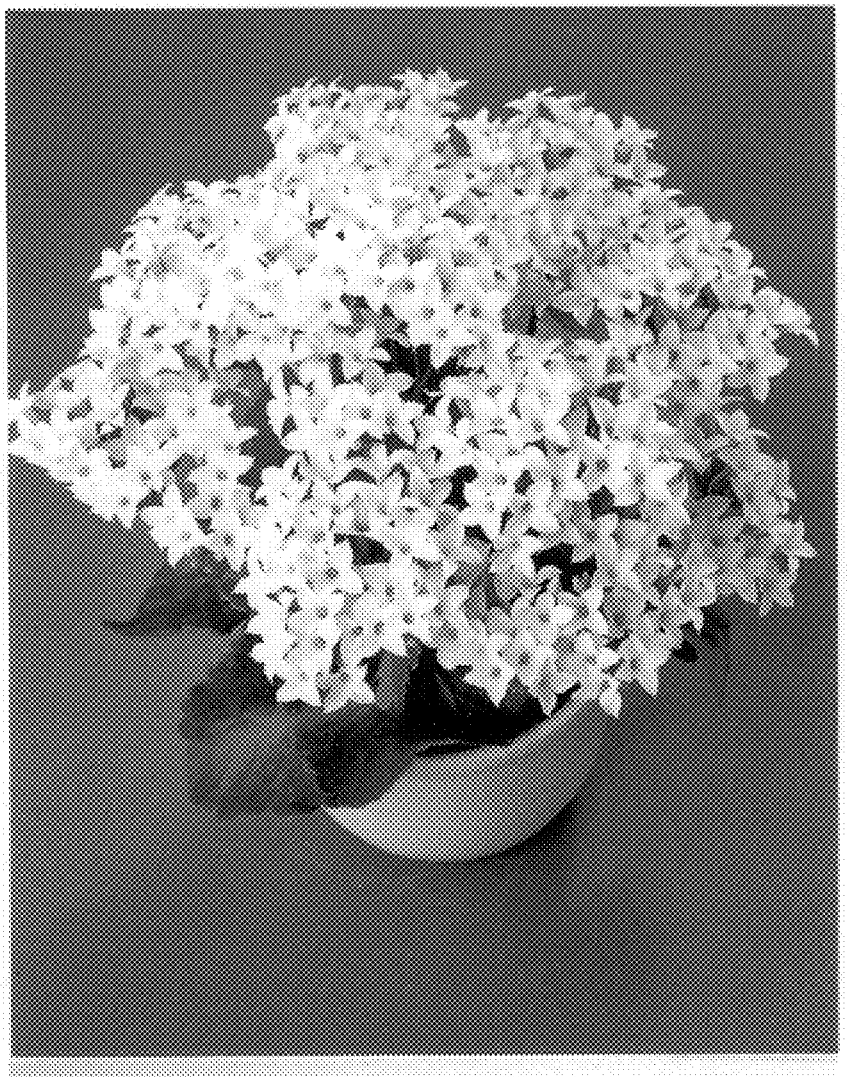
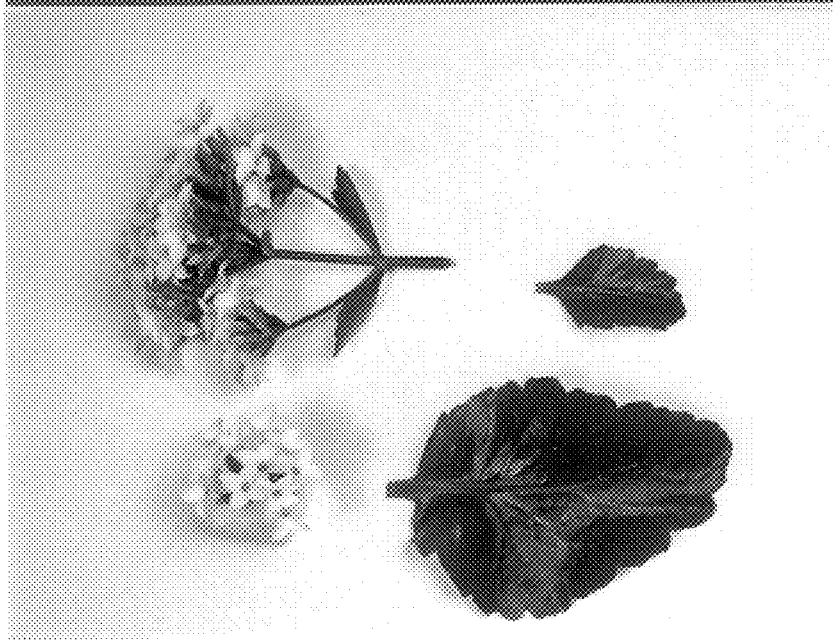

* * * * *